(12) United States Patent
Saavedra et al.

(10) Patent No.: US 6,200,558 B1
(45) Date of Patent: *Mar. 13, 2001

(54) BIOPOLYMER-BOUND NITRIC OXIDE-RELEASING COMPOSITIONS, PHARMACEUTICAL COMPOSITIONS INCORPORATING SAME AND METHODS OF TREATING BIOLOGICAL DISORDERS USING SAME

(75) Inventors: Joseph E. Saavedra, Thurmont; Larry K. Keefer, Bethesda; Peter P. Roller; Miki Akamatsu, both of Rockville, all of MD (US)

(73) Assignee: The United States of America as represented by the Department of Health and Human Services, Washington, DC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/837,812

(22) Filed: Apr. 22, 1997

Related U.S. Application Data

(63) Continuation-in-part of application No. 08/121,169, filed on Sep. 14, 1993, now Pat. No. 5,525,357.

(51) Int. Cl.$^7$ .................. A61K 47/48; A61K 31/395; A61L 27/22

(52) U.S. Cl. ..................... 424/78.08; 424/181.1; 424/78.17; 514/773; 514/611

(58) Field of Search .......................... 424/78.08

(56) References Cited

U.S. PATENT DOCUMENTS

| | | |
|---|---|---|
| 3,153,094 | 10/1964 | Reilly . |
| 4,265,714 | 5/1981 | Nolan et al. . |
| 4,482,533 | 11/1984 | Keith . |
| 4,638,079 | 1/1987 | Inskip et al. . |
| 4,708,854 | 11/1987 | Grinstead . |
| 4,921,683 | 5/1990 | Bedell . |
| 4,952,289 | 8/1990 | Ciccone et al. . |
| 4,954,526 | 9/1990 | Keefer . |
| 4,985,491 | 1/1991 | Ohta et al. . |
| 5,039,705 | 8/1991 | Keefer et al. . |
| 5,087,631 | 2/1992 | Shaffer et al. . |
| 5,087,671 | 2/1992 | Loeppky et al. . |
| 5,094,815 | 3/1992 | Conboy et al. . |
| 5,155,137 | 10/1992 | Keefer et al. . |
| 5,250,550 | 10/1993 | Keefer et al. . |
| 5,405,919 | 4/1995 | Keefer et al. . |
| 5,525,357 * | 6/1996 | Keefer et al. ............ 424/486 |
| 5,632,981 * | 5/1997 | Saavedra ................ 424/78 |
| 5,691,423 * | 11/1997 | Smith et al. ............ 525/377 |
| 5,718,892 * | 2/1998 | Keefer et al. ............ 424/78.27 |

FOREIGN PATENT DOCUMENTS

| | | |
|---|---|---|
| 211789 | 7/1984 | (DE) . |
| 425154-A1 | 10/1990 | (EP) . |
| 469520 | 5/1991 | (EP) . |
| WO 89/12627 | 6/1989 | (WO) . |

OTHER PUBLICATIONS

Lundblad, "Techniques In Protein Modification," 1995, CRC Press, Boca Raton, Florida.

Saavedra JE, Booth MN, Hrabie JA, Davies KM, Keefer LK, "Piperazine As A Linker For Incorporating The Nitric Oxide–Releasing Diazeniumdiolate Group into other biomedically relevant functional molecules," J. Organic Chem., 64 (14), 5124–5131 (Jul. 9, 1999).

Hrabie JA, Saavedra JE, Roller PP, Southan GJ, Keefer LK, "Conversion of proteins to diazeniumdiolate–based nitric oxide donors," *Bioconjugate Chem.*, 10 (5), 838–842 (Sep.–Oct. 1999).

Artysbasheva et al., "Synthesis of 1–Alkoxy–3,3–Dialkyl-triazene 2–Oxides from Alkoxyamines and Nitrosoamines," translates from *Zhurnal Organicheskoi Khimii*, (Journal of Organic Chemistry—U.S.S.R.), 28, (6) 1168–1173 (1987).

Bonakdar et al., "Continuous–Flow Performance of Carbon Electrodes Modifies with Immobilized Fe(II)/Fe(III) Centers," *Calanta*, 36, 219–225 (1989).

DeFeudis, "Endothelium–Dependent Vasorelaxation—A New Basis for Developing Cardiovascular Drugs," *Drugs of Today*, 24 (2), 103–115 (1988).

DeLuca et al., "Parenteral Drug–Delivery Systems," in *Pharmaceutics and Pharmacy Practice*, Banker et al., eds., 238–250 (J.B. Lippincott Co., Philadelphia, PA) (1982).

Drago, "Reactions of Nitrogen(II) Oxide," in *Free Radicals in Organic Chemistry*, Advances in Chemistry Series No. 36, 143–149 (American Chemical Society, Washington DC) (1962).

Drago et al., "The Reaction of Nitrogen(II) Oxide with Various Primary and Secondary Amines," *J. Am. Chem. Soc.*, 83, 1819–1822 (1961).

Furchgott, "The Role of Endothelium in the Responses of Vascular Smooth Muscle to Drugs," *Am. Rev. Pharmacol. Texicol.*, 24, 175–97 (1984).

Garg et al., "Nitric Oxide–Generating Vasodilators Inhibit Mitogenesis and Proliferation of Balb/C 3T3 Fibroblasts by a Cyclic GMP–Independent Mechanism," *Biochem. And Biophys. Res. Comm.*, 171, 474–479 (1990).

(List continued on next page.)

Primary Examiner—Peter F. Kulkosky
(74) Attorney, Agent, or Firm—Leydig, Voit & Mayer, LTD

(57) ABSTRACT

A polymeric composition capable of releasing nitric oxide under physiological conditions which includes a biopolymer, such as a peptide, polypeptide, protein, oligonucleotide or nucleic acid, to which is bound a nitric oxide-releasing $N_2O_2^-$ functional group; pharmaceutical compositions comprising the polymeric composition; and methods of treating biological disorders in which dosage with nitric oxide is therapeutic.

30 Claims, No Drawings

OTHER PUBLICATIONS

Gehlen et al., "Über Reaktionen und Eigenschaften des Stickoxyds und seiner Verbindungen (II.Mitteil): Zur Kenntnis der Salze der Stickoxyd–schwefligen Säure," *Berichte d. D. Chem. Gesellschaft*, LXV, 1130–1140 (1932). ("Reactions and properties of nitric oxide compound of sulfurous acid," *Chemical Abstracts*, 26, 4764–65).

Hansen et al., "N–Nitrosation of Secondary Amines by Nitric Oxide via the 'Drago Comoplex'," in *N–Nitroso Compounds: Occurrence and Biological Effects*, IARC Scientific Publications No. 41, 21–29 (International Agency for Research on Cancer, Lyon, France) (1982).

Hibbs et al., "Nitric Oxide: A Cytotoxic Activated Macrophage Effector Molecule," *Biochem. And Biophys. Res. Comm.*, 157, 87–94 (1988).

Holford et al., "Understanding the Dose–Effect Relationaship: Clinical Application of Pharmacokinetic–Pharmacodynamic Models," *Clinical Pharmacokinetics*, 6, 429–453 (1981).

Ignarro, "Endothelium–Derived Nitric Oxide: Actions and Properties," *The FASEB Journal*, 3, 31–36 (1989).

Ignarro et al., "The Pharmacological and Physiological Role of a Cyclic GMP in Vascular Smooth Muscle Relaxation," *Ann. Rev. Pgarmacol. Toxicol.*, 25, 171–191 (1985).

Ignarro et al., "Mechanism of Vascular Smooth Muscle Relaxation by Organic Nitrates, Nitrites, Nitroprusside and Nitric Oxide: Evidence for theInvolvement of S–Nitrosothiols as Active Intermediates," *J. Pharmacol. Exp. Ther.*, 218, 739–749 (1981).

Ignarro, "Nitric Oxide: A Novel Signal Transduction Mechanism for Transcellular Communication," *Hypertension*, 16, 477–483 (1990).

Ignarro, "Biosynthesis and Metabolism of Endothelium–Derived Nitric Oxide," *Ann. Rev. Pharmacol. Toxicol.*, 30, 535–560 (1990).

Jones, "Metastable Polymers of the Nitrogen Oxides. 1. Open Chain Nitric Oxide Analogues of Polythlazyl: A MNDO/AM1 Study," *J. Phys. Chem.*, 91, 2588–2595 (1991).

Kruszyna et al.., "Red Blood Cells Generate Nitric Oxide from Directly Acting, Nitrogenous Vasodilators," *Toxicol. Appl. Pharmacol.*, 91, 429–438 (1987).

Kuhn et al., "Endothelium–Dependent Vasodilation in Human Epicardial Coronary Arteries: Effect of Prolonged Exposure to Glycerol Trinitrate or SIN–1," *J. Cardiovasc. Pharmacol.*, 14 (Suppl. 11), S47–S54 (1989).

Longhi et al., "Metal–Containing Compounds of the Anion $(C_2H_5)_2NN_2O_2$," *Inorg. Chem.*, 2, 85–88 (1963).

Lutz et al., "Isolation of Trioxodinitrato (II) Complexes of Some First Row Transition Metal Ions," *J.C.S. Chem. Comm.*, 247 (1977).

Maragos et al., "Complexes of •NO with Nucleophiles as Agents for the Controlled Biological Release of Nitric Oxide. Vasorelaxant Effects," *J. Med. Chem.*, 34, 3242–3247 (1991).

Marletta et al., "Unraveling the Biological Significance of Nitric Oxide," *BioFactors*, 2, 219–225 (1990).

Middleton et al., "Further Studies on the Interaction of Nitric Oxide with Transition–Metal Alkyls," *J. Chem. Soc. Dalton*, 1898–1905 (1981).

Myers et al., "Vasorelaxant Properties of the Endothelium–Derived Relaxing Factor More Closely Resemble S–Nitrosocystein than Nitric Oxide," *Nature*, 345, 161–163 (1990).

Palmer et al., "Nitric Oxide Release Accounts for the Biological Activity of Endothelium–Derived Relaxing Factor," *Nature*, 327, 324–327 (1987).

Park et al., "Controlled Protein Release from Polyethyleneimine–Coated Poly(L–lactic Acid)/Pluronic Blend Matrices," *Pharmaceut. Res.*, 9, 37–39 (1992).

Smith et al., "Nitroprusside: A Potpourri of Biologically Reactive Intermediates," in *Advances in Experimental Medicine and Biology*, 283, *Biological Reactive Intermediates IV*, (Witmer et al., eds.), 365–369 (Plenum Press, New York, NY) (1991).

Smith et al., "Complex Contractile Patterns in Canine Colon Produced by Spontaneous Release of Nitric Oxide," *Gastroenterology*, 102, (4) Part 2, A516 (1992).

Stampler et al., "S–Nitrosylation of Proteins with Nitric Oxide: Synthesis and Characterization of Biologically Active Compounds," *Proc. Natl. Acad. Sci. USA*, 89, 444–448 (1992).

Stampler et al., "S–Nitrosylation of Tissue–Type Plasminogen Activator Confers Vasodilatory and Antiplatelet Properties on the Enzyme," *Proc. Natl. Acad. Sci. USA*, 89: 8087–8091 (1992).

Stuehr et al., "Nitric Oxide: A Macrophage Product Responsible for Cytostasis and Respiratory Inhibition in Tumor Target Cells," *J. Exp. Med.*, 169, 1543–1555 (1989).

Trissel, "Intravenous Infusion Solutions," *Handbook on Injectable Drugs*, $4^{th}$ ed., 622–629 (American Society of Hospital Pharmacists, Bethesda, MD) (1986).

Weitz et al., "Zur Kenntnis der stickoxyd–schwefligen Säure (II.Mitteil)," *Berichte d. D. Chem. Gesellschafte*, LXVI, 1718–1727 (1933). ("Nitrosylsulfuric acid," *Chemical Abstracts*, 28, 2636.).

WHO Task Group on Environmental Health Criteria for Oxides of Nitrogen, *Environmental Health Criteria 4: Oxides of Nitrogen*, (World Health Organization, Geneva) (1977).

Wilcox et al., "Effect of Cyanide on the Reaction of Nitroprusside with Hemoglobin: Relevance to Cyanide Interference with the Biological Activity of Nitroprusside," *Chem. Res. Toxicol.*, 3, 71–76 (1990).

Off–Line Bibliographic Citation List Generated by *Medlars II* regarding :Nitric:Release: or :Release:Nitric: (Excludes Proteins/Peptides (MH).

Off–Line Bibliographic Citation List Generated by *Medlars II* regarding Nitric Oxide/Proteins/:Nitric:Release: or : Release:Nitric: (SENS).

Off–Line Bibliographic Citation List Generated by *Medlars II* regarding :Nitric:Donor: or :NO:Donor: (SENS).

Off–Line Bibliographic Citation List Generated by *Medlars II* regarding Nitric Oxide/Peptides/:Nitric:Release: or : Release:Nitric.

Dialog Search Report regarding Nitric Oxide Complex(es).

Dialog Search Report regarding Nitric Oxide and Releas?.

Dialog Search Report regarding Nononate(s).

J.S. Stamler et al Proc. Natl. Acad. Sci. vol. 89, pp. 444–448, Jan. 1992.*

O. Mascarenhas UMI Dec. 1993 Dissertation pp. 56–62, 74–81.*

Mitchell et al Biochemistry 1990 29, 2802–2807.*

\* cited by examiner

BIOPOLYMER-BOUND NITRIC OXIDE-RELEASING COMPOSITIONS, PHARMACEUTICAL COMPOSITIONS INCORPORATING SAME AND METHODS OF TREATING BIOLOGICAL DISORDERS USING SAME

RELATED APPLICATION

This is a continuation-in-part of U.S. Ser. No. 08/121,169, filed Sep. 14, 1993 (now U.S. Pat. No. 5,525,357, issued Jun. 11, 1996). The entire disclosure of the '169 application is incorporated herein by reference.

TECHNICAL FIELD OF THE INVENTION

The present invention relates to polymeric compositions capable of releasing nitric oxide. In particular, the present invention relates to polymeric compositions comprising a biopolymer, such as a peptide, polypeptide, protein, oligonucleotide, nucleic acid, or the like to which is bound a nitric oxide-releasing $N_2O_2^-$ functional group, pharmaceutical compositions comprising such polymeric compositions, and methods of treating biological disorders with such a biopolymeric composition.

BACKGROUND OF THE INVENTION

Nitric oxide (NO) has recently been implicated in a variety of bioregulatory processes, including normal physiological control of blood pressure, macrophage-induced cytostasis and cytotoxicity, and neurotransmission (Moncada et al., "Nitric Oxide from L-Arginine: A Bioregulatory System," *Excerpta Medica*, International Congress Series 897 (Elsevier Science Publishers B.V.: Amsterdam, 1990); Marletta et al., "Unraveling the Biological Significance of Nitric Oxide," *Biofactors*, 2, 219–225 (1990); Ignarro, "Nitric Oxide. A Novel Signal Transduction Mechanism for Transcellular Communication," *Hypertension* (Dallas), 16, 477–483 (1990)). A number of compounds have been developed which are capable of delivering nitric oxide, including compounds which release nitric oxide upon being metabolized and compounds which release nitric oxide spontaneously in aqueous solution.

Those compounds which release nitric oxide upon being metabolized include the widely used nitrovasodilators glyceryl trinitrate and sodium nitroprusside (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990). Another compound, S-nitroso-N-acetylpenicillamine, has been reported to release nitric oxide in solution and to be effective at inhibiting DNA synthesis (Garg et al., *Biochem. and Biophys. Res. Comm.*, 171, 474–479 (1990)).

Numerous nitric oxide-nucleophile complexes have been described, e.g., Drago, *ACS Adv. Chem. Ser.*, 36, 143–149 (1962). See also Longhi and Drago, *Inorg. Chem.*, 2, 85 (1963). Some of these complexes are known to evolve nitric oxide on heating or hydrolysis, e.g., Maragos et al., *J. Med. Chem.* 34, 3242–3247 (1991).

The cytostatic effect of nitric oxide solutions on tumor cells in vitro has been demonstrated. In particular, it has been shown that solutions of nitric oxide inhibit DNA synthesis and mitochondrial respiration of tumor cells in vitro (Hibbs et al., *Biochem. and Biophys. Res. Comm.*, 157, 87–94 (1988); Stuehr et al., *J. Exp. Med.*, 169, 1543–1555 (1989)).

Endothelium-derived relaxing factor (EDRF) is a labile humoral agent which is part of a cascade of interacting agents involved in the relaxation of vascular smooth muscle. EDRF is thus important in the control of vascular resistance to blood flow and in the control of blood pressure. Some vasodilators act by causing EDRF to be released from endothelial cells. (See Furchgott, *Ann. Rev. Pharmacol. Toxicol.*, 24, 175–197 (1984).) In 1987, Palmer et al., presented evidence that EDRF is identical to the simple molecule, nitric oxide, NO (*Nature*, 317, 524–526 (1987)), though more recently, that conclusion has been challenged (Myers et al., *Nature*, 345, 161–163, 1990)).

Nitric oxide in its pure form, however, is a highly reactive gas having limited solubility in aqueous media (WHO Task Group on Environmental Health Criteria for Oxides of Nitrogen, *Oxides of Nitrogen*, Environmental Health Criteria 4 (World Health Organization: Geneva, 1977)). Nitric oxide, therefore, is difficult to introduce reliably into most biological systems without premature decomposition.

The difficulty in administering nitric oxide can be overcome in some cases by administering nitric oxide pharmacologically in prodrug form. The compounds glyceryl trinitrate and sodium nitroprusside are relatively stable and release nitric oxide only on activation (Ignarro et al., *J. Pharmacol. Exp. Ther.*, 218, 739–749 (1981); Ignarro, *Annu. Rev. Pharmacol. Toxicol.*, 30, 535–560 (1990); Kruszyna et al., *Toxicol. Appl. Pharmacol.*, 91, 429–438 (1987); Wilcox et al., *Chem. Res. Toxicol.*, 3, 71–76 (1990)). While this feature may be an advantage in some applications, it can also be a significant liability, as in the development of tolerance to glyceryl trinitrate via the exhaustion of the relevant enzyme/cofactor system (Ignarro et al., *Annu. Rev. Pharmacol. Toxicol.*, 25, 171–191 (1985); Kuhn et al., *J. Cardiovasc. Pharmacol.*, 14 (Suppl. 11), S47–S54 (1989)) and toxicity from metabolically produced cyanide during prolonged administration of nitroprusside (Smith et al., "A Potpourri of Biologically Reactive Intermediates" in *Biological Reactive Intermediates IV. Molecular and Cellular Effects and Their Impact on Human Health* (Witmer et al., eds.), Advances in Experimental Medicine and Biology Volume 283 (Plenum Press: New York, 1991), pp. 365–369).

Evidence that nitric oxide is released from the endothelial cells and is responsible for the relaxation of the vascular smooth muscle, and hence the control of blood pressure, has resulted in the development of artificial agents that can deliver nitric oxide in vivo. A very important class of such agents is the nitric oxide-nucleophile complexes. Recently, a method for treating cardiovascular disorders in a mammal with certain nitric oxide-nucleophile complexes was disclosed, e.g. in U.S. Pat. No. 4,954,526. These compounds contain the anionic $N_2O_2^-$ group or derivatives thereof. See also, Maragos et al., *J. Med. Chem.*, 34, 3242–3247 (1991). Many of these compounds have proven especially promising pharmacologically because, unlike nitrovasodilators such as nitroprusside and nitroglycerin, they release nitric oxide without first having to be activated. The only other series of drugs currently known to be capable of releasing nitric oxide purely spontaneously is the S-nitrosothiol series, compounds of structure R—S—NO (Stamler et al., *Proc. Natl. Acad. Sci. U.S.A.*, 89, 444–448 (1992); Stamler et al., *Proc. Natl. Acad. Sci. U.S.A.*, 89, 8087–8091 (1992)); however, the R—S→NO—NO reaction is kinetically complicated and difficult to control (Morley et al., *J. Cardiovasc. Pharmacol.*, 21, 670–676 (1993)). The $N_2O_2^-$ containing compounds are thus advantageous among drugs currently known in that they decompose at any given pH via a cleanly first order reaction to provide doses of nitric oxide that can be predicted, quantified, and controlled. See, e.g., Maragos et al., *J. Med. Chem.*, 34, 3242–3247 (1991).

Nitric oxide/nucleophile complexes which release nitric oxide in aqueous solution are also disclosed in U.S. Pat. Nos. 5,039,705, 5,185,376, 5,155,137, 5,208,233, 5,212,204, 5,250,550 and 5,366,997 (issue date Nov. 22, 1994) as well as in pending U.S. patent applications Ser. Nos. 07/764,908 (filed Sep. 24, 1991), (now abandoned) 07/858,885 (filed Mar. 27, 1992) (now U.S. Pat. No. 5,389,675, issued Feb. 14, 1995), 07/867,759 (filed Apr. 13, 1992) (now abandoned), 07/935,565 (filed Aug. 24, 1992) (now U.S. Pat. No. 5,405,919, issued Apr. 11, 1995), 08/017,270 (filed Feb. 12, 1993) (now abandoned), and 08/121,169 (filed Sep. 14, 1993) (now U.S. Pat. No. 5,525,357, issued Jun. 11, 1996) as useful therapeutic agents (see also Maragos et al., *J. Med. Chem.*, 34, 3242–3247 (1991)).

Despite the promise of the nitric oxide/nucleophile adducts that have been investigated, their pharmacological application has been limited by their tendency to distribute evenly throughout the medium. Such even distribution is a great advantage in many research applications, but tends to compromise their selectivity of action. Another limitation to the application of these nitric oxide/nucleophile adducts is their propensity for relatively rapid release of nitric oxide which may necessitate frequent dosing to achieve a prolonged biological effect. Thus there remains a need for nitric oxide-releasing compositions which are capable of concentrating the effect of the nitric oxide release to a situs of application and for which nitric oxide release may be controlled for effective dosing.

It is, therefore, a principal object of the present invention to provide a polymeric composition comprising a biopolymer to which is bound a $N_2O_2^-$ functional group and which is capable of releasing NO under physiological conditions. Another object of the invention is to provide a polymeric composition comprising a biopolymer to which is bound a $N_2O_2^-$ functional group whose release of NO can be controlled such that local or cell/tissue specific release can be effected. It is another object of the present invention to provide a polymeric composition comprising a biopolymer to which is bound a $N_2O_2^-$ functional group whose release of NO is such that a prolonged biological effect can be attained. Yet another object of the present invention is to provide pharmaceutical compositions comprising such biopolymeric compositions. It is also an object of the present invention to provide a method of treating a biological disorder involving the administration of such biopolymeric compositions. These and other objects and advantages of the present invention, as well as additional inventive features, will be apparent from the description of the invention provided herein.

BRIEF SUMMARY OF THE INVENTION

The present invention provides a polymeric composition capable of spontaneously releasing nitric oxide under physiological conditions. The polymeric composition comprises a biopolymer to which is bound a nitric oxide-releasing $N_2O_2^-$ functional group. "Biopolymer(ic)" is meant to include any biological polymer, such as peptides, polypeptides, proteins, oligonucleotides, and nucleic acids, including those that contain naturally occurring and/or nonnaturally occurring subunits. Specific examples include antibodies or fragments thereof and peptide hormones, proteins, and growth factors for which the target cell type has a high population of receptors. The preferred nitric oxide-releasing $N_2O_2^-$ functional group which is used to form the biopolymer-bound NONOates of the present invention is defined by the formula:

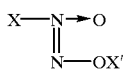

wherein X is an organic or inorganic moiety and X' may be the same as X, or it may be a pharmaceutically acceptable metal center, a pharmaceutically acceptable cation, or the like. The $N_2O_2^-$ group is bonded to the biopolymer through either or both the linking groups X and X'.

By "bound to a polymer," it is meant that the $N_2O_2^-$ functional group is associated with, part of, incorporated with or contained within the biopolymer physically or chemically. Bonding of the $N_2O_2^-$ functional group to the polymer can be achieved by covalent bonding of the $N_2O_2^-$ group to the biopolymer through a linking group X or X'. Chemical bonding of the $N_2O_2^-$ functional group to the biopolymer may be by, for example, covalent bonding of the linking group X or X' to the biopolymer such that the linking group forms part of the biopolymer itself, i.e., is in the biopolymer backbone or is attached to pendant groups on the biopolymer backbone. The manner in which the nitric oxide-releasing $N_2O_2^-$ functional group is associated with, part of, incorporated with or contained within, i.e., "bound," to the polymer is inconsequential to the present invention and all means of association, incorporation and bonding are contemplated herein.

In another aspect of the invention, the biopolymer-bound nitric oxide-releasing compositions of the present invention can be bound to or physically associated with polymers that are not biopolymers (referred to hereinafter as "non-biopolymers").

The present invention also provides a pharmaceutical composition which includes a pharmaceutically acceptable carrier and a polymeric composition comprising a biopolymer to which is bound a nitric oxide-releasing $N_2O_2^-$ functional group.

The invention further provides a method of treating biological disorders in which dosage with nitric oxide would be therapeutic which comprises administering to a mammal afflicted with such a biological disorder a polymeric composition, comprising a biopolymer to which is bound a nitric oxide-releasing $N_2O_2^-$ functional group, in an amount sufficient to release a therapeutically effective amount of nitric oxide.

DETAILED DESCRIPTION OF THE PREFERRED EMBODIMENTS

The present invention is predicated on the discovery that useful pharmacological agents can be provided by incorporating nitric oxide-releasing $N_2O_2^-$ functional groups into a biopolymer. Accordingly, the $N_2O_2^-$ functional group is "bound to the polymer" as that term has been defined herein. The term NONOate is used herein as a shorthand to refer to the nitric oxide-releasing $N_2O_2^-$ group.

It has been discovered that incorporation of a NONOate into a biopolymer provides a biopolymer-bound NONOate composition that can be applied with specificity to a biological site of interest. Site specific application of the biopolymer-bound NONOate enhances the selectivity of action of the nitric oxide-releasing NONOate. If $N_2O_2^-$ functional groups attached to the biopolymer are necessarily localized, then the effect of their nitric oxide release will be concentrated in the tissues with which they are in contact. If the biopolymer is soluble, selectivity of action can still be arranged, for example, by attachment to or derivatization of an antibody specific to the target tissue. Similarly, attachment of $N_2O_2^-$ groups to small peptides that mimic the recognition sequences of ligands for important receptors provides localized concentrated effect of nitric oxide release, as would attachment to oligonucleotides capable of site-specific interactions with target sequences in a nucleic acid. Other proteins, peptides, polypeptides, nucleic acids and polysaccharides, including hormones and motility, chemotactic and extravasating factors or agents, can be similarly utilized.

By way of illustration, a piperazine monoNONOate derivative can be covalently attached to a polypeptide containing the IKVAV recognition sequence important in tumor cell chemotaxis. Through retention of both the capacity to regenerate NO as an antichemotactic agent and the affinity of the IKVAV sequence for tumor cells and/or sites in the vascular and lymphatic systems where the tumor cells tend to attach, metastasis can be reduced or even prevented.

While not being bound to any particular theory, it is believed that longevity of nitric oxide release in the biopolymer-bound NONOate compositions of the present invention is to be attributed both to the physical structure of the composition and to electrostatic effects. Thus, it is believed that if the biopolymer is an insoluble solid, $N_2O_2^-$ groups near the surface of the particle should be available for rapid release while those that are more deeply imbedded are sterically shielded, requiring more time and/or energy for the nitric oxide to work its way into the medium. Unexpectedly, it has been found that increasing positive charge in the vicinity of an $N_2O_2^-$ functional group also tends to increase the halflife of nitric oxide generation. The mechanism of this rate retardation may be attributable simply to repulsive electrostatic interactions, i.e., increasing the number of $H^+$-repelling positive charges in the vicinity of the $N_2O_2^-$ groups inhibits attack of positively charged $H^+$ ions on the $N_2O_2^-$ functional group and slows the rate of its $H^+$-catalyzed decomposition. For example, by attaching amino groups to the polymeric support that are capable of forming the nitric oxide-releasing $N_2O_2^-$ functional group on reaction with nitric oxide, partially converted structures can be produced on less-than-exhaustive treatment with nitric oxide that after exposure to water contain a large number of positively charged ammonium centers surrounding the $N_2O_2^-$ group that electrostatically inhibit the approach of $H^+$ ions capable of initiating nitric oxide loss from the nitric oxide-releasing $N_2O_2^-$ functional group.

The nitric oxide-releasing $N_2O_2^-$ functional groups that are bound to the biopolymer generally are capable of releasing nitric oxide in an aqueous environment spontaneously upon contacting an aqueous environment, i.e., they do not require activation through a redox reaction or electron transfer such as is required for glyceryl trinitrate and sodium nitroprusside. Some of the nitric oxide/nucleophile complexes useful in the context of the present invention do require activation by particular means, but only as necessary to free the nitric oxide-releasing $X[N(O)NO]^-$ group in the vicinity of the particular cells of interest. As an example, covalent attachment of a protecting group to the anionic $[N(O)NO]^-$ function provides a means of postponing nitric oxide release until the molecule reaches an organ capable of metabolically removing the protecting group. By choosing a protecting group that is selectively cleaved by enzymes specific to a tumor, biological disorder, cell, or tissue of interest, for example, the action of the nitric oxide/nucleophile complex can be targeted to maximize the desired effect. While the biopolymer-bound NONOate compositions of the present invention are capable of releasing nitric oxide in an aqueous solution, such a compound preferably releases nitric oxide under physiological conditions.

For example, a NONOate functionality can be attached to a tumor-specific antibody or other protein which has one or more lysine side chain amino groups that are unnecessary to the function of the protein by reacting said lysine group(s) with a derivatizing agent capable of covalently attaching first to the lysine amino nitrogen then in a subsequent step to the sulfur atom of an O-functionalized NONOate containing a free thiol grouping elsewhere in the molecule. Once such a protein arrives at the desired target tissue after systemic application, enzymatic or hydrolytic removal of the substituent bound to oxygen frees the anionic NONOate function to concentrate NO release at that site.

The preferred nitric oxide-releasing $N_2O_2^-$ functional group which is used to form the biopolymer-bound NONOates of the present invention is defined by the formula:

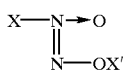

wherein X is an organic or inorganic moiety and X' is an organic or inorganic substituent, a pharmaceutically acceptable metal center, a pharmaceutically acceptable cation, or the like. The $N_2O_2^-$ group is bonded to the biopolymer through either or both the linking groups, X and X'.

The nitric oxide-releasing $N_2O_2^-$ functional group is preferably a nitric oxide/nucleophile adduct, e.g., a complex of nitric oxide and a nucleophile, most preferably a nitric oxide/nucleophile complex which contains the anionic moiety $X[N(O)NO]^-$, where X is any suitable nucleophile residue. The nucleophile residue is preferably that of a primary amine (e.g., $X=(CH_3)_2CHNH$, as in $(CH_3)_2CHNH[N(O)NO]Na$), a secondary amine (e.g., $X=(CH_3CH_2)_2N$, as in $(CH_3CH_2)_2N[N(O)NO]Na$), a polyamine (e.g., X=spermine, as in the zwitterion $H_2N(CH_2)_3NH_2^+(CH_2)_4N[N(O)NO]^-(CH_2)_3NH_2$, X=2-(ethylamino)ethylamine, as in the zwitterion $CH_3CH_2N[N(O)NO]^-CH_2CH_2NH_3^+$, or X=3-(n-propylamino)propylamine, as in the zwitterion $CH_3CH_2CH_2N[N(O)NO]^-CH_2CH-CH_2NH_3^+$), or oxide (i.e., $X=O^-$, as in $NaO[N(O)NO]Na$), or a derivative thereof. Such nitric oxide/nucleophile complexes are capable of delivering nitric oxide in a biologically usable form at a predictable rate.

Other suitable nitric oxide/nucleophile complexes include those having the following formulas:

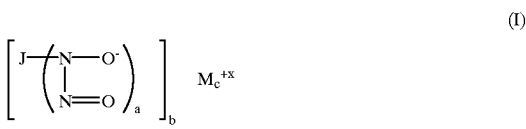

wherein J is an organic or inorganic moiety, $M^{+x}$ is a pharmaceutically acceptable cation, where x is the valence of the cation, a is an integer of at least one, and b and c are the smallest integers that result in a neutral compound, as described in U.S. Pat. No. 5,208,233, and incorporated herein by reference;

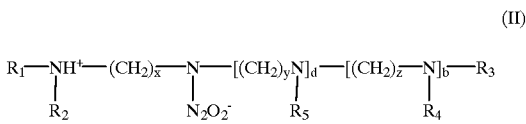

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12, as described in U.S. Pat. No. 5,155,137, incorporated herein by reference;

(III)

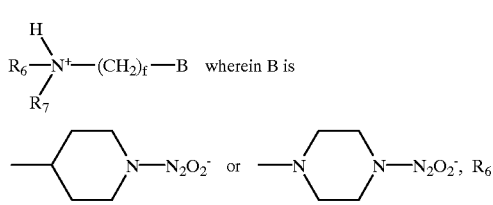  wherein B is and $R_7$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

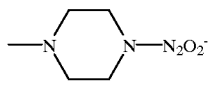

then f is an integer from 2 to 12, as described in U.S. Pat. No. 5,155,137, incorporated herein by reference;

(IV)

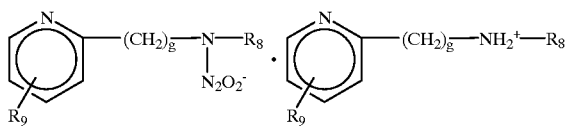

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, $R_9$ is hydrogen or a $C_{1-12}$ straight or branched chain alkyl, and g is 2 to 6, as described in U.S. Pat. No. 5,250,550, incorporated herein by reference;

(V)

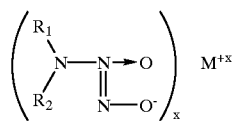

wherein $R_1$ and $R_2$ are independently selected from the group consisting of a straight chain or branched chain $C_1$–$C_{12}$ alkyl group and a benzyl group, or else $R_1$ and $R_2$, together with the nitrogen atom, are bonded to form a heterocyclic group, preferably a pyrrolidino, piperidino, piperazino or morpholino group, $M^{+x}$ is a pharmaceutically acceptable cation, and x is the valence of the cation, as described in U.S. Pat. Nos. 5,039,705 and 5,208,233 and U.S. patent application Ser. No. 08/017,270, filed Feb. 12, 1993, (now abandoned) and incorporated herein by reference;

$$K[(M)_x{}^{x'}(L)_y(R^1R^2N\text{-}N_2O_2)_z]$$ (VI)

wherein M is a pharmaceutically acceptable metal, or, where x is at least two, a mixture of two different pharmaceutically acceptable metals, L is a ligand different from ($R^1R^2N$-$N_2O_2$) and is bound to at least one metal, $R^1$ and $R^2$ are each organic moieties and may be the same or different, x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary, as described in U.S. patent application Ser. No. 07/858,885, filed Mar. 27, 1992(now U.S. Pat. No. 5,389,675, issued Feb. 14, 1995), and incorporated herein by reference;

$$[R\text{—}N\,(H)\,N(NO)\,O\text{—}]_yX$$ (VII)

wherein R is $C_{2-8}$ lower alkyl, phenyl, benzyl, or $C_{3-8}$ cycoloalkyl, any of which R groups may be substituted by one to three substituents, which are the same or different, selected from the group consisting of halo, hydroxy, $C_{1-8}$ alkoxy, —$NH_2$, —C (O)$NH_2$, —CH (O), —C(O)OH, and —$NO_2$, X is a pharmaceutically acceptable cation, a pharmaceutically acceptable metal center, or a pharmaceutically acceptable organic group selected from the group consisting of $C_{1-8}$ lower alkyl, —C(O)$CH_3$, and —C(O)$NH_2$, and y is one to three, consistent with the valence of X, as described in U.S. Pat. No. 4,954,526 and incorporated herein by reference; and (VIII)

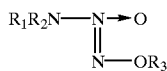

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, preferably a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —$(CH_2)_n$—ON=N(O)$NR_1R_2$, wherein n is an integer of 2–8, and $R_1$ and $R_2$ are as defined above; with the proviso that $R_1$, $R_2$ and $R_3$ do not contain a halo or a hydroxy substituent α to a heteroatom, as described in U.S. Application Ser. No. 07/950,637, filed Sep. 23, 1992 (now U.S. Pat. No. 5,366,997, issued Nov. 22, 1994).

Any of a wide variety of biopolymers can be used in the context of the present invention. Biopolymers suitable for use include peptides, polypeptides, proteins, oligonucleotides, nucleic acids, e.g., RNA and DNA, antibodies, peptide hormones, glycoproteins, glycogen, and the like. Alternatively, a subunit of a biopolymer, such as a fatty acid, glucose, an amino acid, a succinate, a ribonucleotide, a ribonucleoside, a deoxyribonucleotide, and a deoxyribonucleoside can be used. Illustrative examples include antibodies or fragments thereof; extracellular matrix proteins such as laminin, fibronectin, or their cell attachment-site peptide recognition sequences, such as RGDS, IKVAV, YIGSR, and the like; and growth factors, peptide hormones, and other polypeptides for which there are high-affinity cell surface receptor sites, such as EGF, TGFα, TGFβ and TNF. Such molecules, upon receptor binding, may be internalized into the target cells, thereby facilitating intracellular delivery of the NO donor moiety.

The nitric oxide-releasing $N_2O_2^-$ functional groups may be bound to the biopolymer by formation of a nitric oxide/nucleophile complex of the type and having the formulas of those described above, in situ on the biopolymer. The $N_2O_2^-$ functional group may be attached to an atom in the backbone of the biopolymer, or it may be attached to a group pendant to the biopolymer backbone, or it may simply be entrapped in the biopolymer matrix. Where the $N_2O_2^-$ functional group is attached to the biopolymer backbone, the biopolymer includes in its backbone sites which are capable of reacting with nitric oxide to bind the nitric oxide for future release. For example, the biopolymer can include nucleophilic nitrogen atoms which react with nitric oxide to form the $N_2O_2^-$ functional group at the nitrogen in the backbone. Where the $N_2O_2^-$ functional group is a group pendant to the polymer backbone, the biopolymer contains, or is derivatized with, a suitable pendant nucleophile residue capable of reacting with nitric oxide to form the $N_2O_2^-$ functionality. Reaction of the biopolymer which contains a suitable nucleophilic residue, or of the suitably derivatized biopolymer, with nitric oxide thus provides a biopolymer-bound nitric oxide-releasing $N_2O_2^-$ functional group.

To form the biopolymer-bound nitric oxide releasing $N_2O_2^-$ functional group, it is generally preferred to impart a net charge to the polymer near the site on the biopolymer where the $N_2O_2^-$ functional group is to be formed. By way of illustration, several general means are available for synthesizing a biopolymeric composition comprising a biopolymer to which is attached a NONOate functional group. As one example, an ion of structure $X-N_2O_2^-$ is reacted with an electrophilic agent (an $[X']^+$-donor) to generate a covalently bonded NONOate of formula X—N(O)=NOX'; this protected complex is then attached to the desired biopolymer via the nucleophile residue, X, or the electrophile residue, X'. Alternatively, a nucleophile residue that is already part of (or that can be attached to) the biopolymer can be reacted with NO under basic conditions to give a nitric oxide complex containing a $N_2O_2^-$ functional group. As a specific example, a simple amino acid bearing a secondary amino group can be reacted with nitric oxide to generate a compound in accordance with the present invention. Similarly, the NONOate functionality can be attached to a basic nitrogen in a peptide. Alternative means can be used to attach NONOate-containing molecules to thiol or activated carboxylic acid groups in a peptide, polypeptide or protein in accordance with the present invention.

Further, by way of illustration, the $N_2O_2^-$ functional group may be attached to a peptide such as arg-gly-asp (RGD), to prepare the molecule arg-gly-asp-[N(O)NO]$^-$. Preferably, the RGD tripeptide would be attached to the NONOate through a linking group such as additional peptide units. Other receptor/ligand recognition sequences may be used analogously.

The biopolymer-bound nitric oxide-releasing compositions of the present invention will find utility in a wide variety of applications and in a wide variety of forms depending on the biological disorder to be treated. For example, the biopolymer-bound NONOate may itself be structurally sufficient to serve as implants, patches, stents, liposomes, microparticles, microspheres, beads, powders, liquids, gels, monolithic resins, disks, or the like, or the biopolymer-bound NONOate can be attached to a non-biopolymer, or the like, suitable for such purpose. The term non-biopolymer is used herein to mean any polymer that is not a biopolymer. Further, by way of illustration, the biopolymer-bound NONOate composition can be incorporated into other polymer matrices, substrates or the like, or it may be microencapsulated, or the like.

The biopolymer-bound nitric oxide/nucleophile compositions of the present invention have a wide range of biological utility. In view of the growing awareness that nitric oxide is an especially versatile and important bioeffector species, having been implicated mechanistically in such critical bodily functions as vasorelaxation, neurotransmission and the immunological response (Moncada et al., *Pharmacol. Rev.*, 43, 109–142 (1991), the compositions of the present invention find utility in applications where nitric oxide release is needed. For example, the biopolymer-bound NONOates may be used to reduce the risk of restenosis after angioplasty.

The following are further illustrative of, and not in any way in limitation of, the broad uses and applications of the biopolymer-bound compositions of this invention. Thus, for example, in view of dramatic but short-lived pulmonary vaso- and bronchodilatory properties exhibited by nitric oxide (Roberts et al., *Circulation* (Suppl. II), 84, A1279 (1991)), administration of biopolymer-bound nitric oxide/nucleophile adduct compositions into the lungs in aerosolized form may be used in treating a variety of pulmonary disorders. Since natural, endogenous nitric oxide has been identified as an effector of penile erection (Blakeslee, New York Times, Jan. 9, 1992, page A1), the biopolymer-bound nitric oxide/nucleophile adduct compositions of the present invention may be incorporated into suitable penile implants, preparations for transurethral injection, dermal patches or condoms for treatment of impotence in men. The ability of certain monomeric nitric oxide/nucleophile adducts to inhibit platelet aggregation coupled with their demonstrated cytostatic activity allows for an invaluable two-pronged approach to prevention of restenosis following angioplasty; stents fabricated with polymer-bound nitric oxide-releasing $N_2O_2^-$ functional group compositions may be used both to inhibit cell division in areas with damaged endothelium and to prevent adhesion of platelets at these locations as well, minimizing the risk of recurring blockage. With an inverse relationship between generation of nitric oxide by tumor cells and their metastatic potential having been proposed (Radomski et al., *Cancer Res.*, 51, 6073–6078 (1991), polymer-bound nitric oxide/nucleophile compositions can be used to reduce the risk of metastasis in cancer patients. Similarly, it is contemplated that the biopolymer-bound nitric oxide-releasing compositions of the present invention can be used to coat prostheses and medical implants, such as breast implants, prior to surgical connection to the body as a means of reducing the risk of solid state carcinogenesis associated therewith. Tumor-specific antibodies containing the $N_2O_2^-$ functional group can be used to sensitize cancer cells to radiotherapy. The $N_2O_2^-$ functional group can be attached to hormones that concentrate in the uterus, where the release of NO can halt premature labor. With nitric oxide being additionally implicated in gastric motility, neurotransmission, nociception, and other natural roles, the compositions of this invention can be used for those applications as well.

In another aspect of the invention, there is provided a polymer-bound nitric oxide-releasing composition which comprises the novel biopolymer-bound nitric oxide-releasing compositions of the present invention and a non-biopolymer as disclosed in copending application Ser. No. 07/935,565. In accordance with this aspect of the invention, the biopolymer-bound NONOates described herein are incorporated into or bonded to a non-biopolymer. For this use, any of a wide variety of polymers can be used. It is only necessary that the polymer selected is biologically acceptable. Illustrative of polymers suitable for use in the present invention are polyolefins, such as polystyrene, polypropylene, polyethylene, polytetrafluorethylene, polyvinylidene difluoride, and polyvinylchloride, polyethylenimine or derivatives thereof, polyethers such as polyethyleneglycol and polysaccharides, polyesters such as poly(lactide/glycolide), polyamides such as nylon, polyurethanes, colestipol and derivatives thereof. The biopolymeric nitric oxide-releasing compositions described above may be bound to a non-biopolymer support in a number of different ways. For example, the biopolymer-bound NONOates may be bound to the non-biopolymer by coprecipitation of the biopolymer with the non-biopolymer. Coprecipitation involves, for example, solubilizing both the non-biopolymer and the biopolymer-bound NONOate and evaporating the solvent. Alternatively, the biopolymer-bound NONOates can be chemically bonded to the non-biopolymer.

The physical and structural characteristics of the non-biopolymers suitable for use in the present invention are not narrowly critical, but rather will depend on the end use application. It will be appreciated by those skilled in the art that where the resulting polymeric composition is intended for topical, dermal, percutaneous, or similar use, it need not be biodegradable. For some uses, such as ingestion or the like, it may be desirable that the non-biopolymer slowly dissolve in a physiological environment or that it is biodegradable. The resulting polymeric forms can be bioerodible, durable or instantly soluble in physiological fluids.

One skilled in the art will appreciate that suitable methods of administering the biopolymer-bound nitric oxide-releasing $N_2O_2^-$ functional group compositions of the present invention to an animal are available, and, although more than one route can be used to administer a particular composition, a particular route can provide a more immediate and more effective reaction than another route. Pharmaceutically acceptable carriers are also well-known to those who are skilled in the art. The choice of carrier will be determined in part by the particular composition, as well as by the particular method used to administer the composition. Accordingly, there is a wide variety of suitable formulations of the pharmaceutical composition of the present invention.

Formulations suitable for oral administration can consist of (a) liquid solutions, such as an effective amount of the biopolymer-bound composition dissolved in diluents, such as water or saline, (b) capsules, sachets or tablets, each containing a predetermined amount of the active ingredient, as solids or granules, (c) suspensions in an appropriate liquid, and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible carriers. Lozenge forms can comprise the active ingredient in a flavor, usually sucrose and acacia or tragacanth, as well as pastilles comprising the active ingredient in an inert base, such as gelatin and glycerin or sucrose and acacia emulsions, gels, and the like containing, in addition to the active ingredient, such carriers as are known in the art.

The biopolymer-bound nitric oxide-releasing compositions of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid carrier, for example, water, for injections, immediately prior to use. Extemporaneous injection solutions and suspensions can be prepared from sterile powders, granules, and tablets of the kind previously described.

The dose administered to an animal, particularly a human, in the context of the present invention should be sufficient to effect a therapeutic response in the animal over a reasonable time frame. The dose will be determined by the strength of the particular compositions employed and the condition of the animal, as well as the body weight of the animal to be treated. The size of the dose also will be determined by the existence, nature, and extent of any adverse side-effects that might accompany the administration of a particular composition.

The following examples further illustrate the present invention, but do not limit the scope thereof.

In the Examples, chemiluminescence analysis for total recoverable nitric oxide from polymers containing the nitric oxide-releasing $N_2O_2^-$ functional group by acid treatment was carried out as follows:

The analysis of NO adducts, i.e., polymers containing the nitric oxide-releasing $N_2O_2^-$ functional group, was done on a nitric oxide analyzer and was patterned after the procedure of Maragos et al., *J. Med. Chem.*, 34, 3242–3247 (1991). A reactor vessel fitted with a septum was charged with a small aliquot of the polymer to be studied and the system was purged with helium for several minutes to remove traces of oxygen. Two milliliters of 10 mM sulfuric acid was added by injection through the septum to begin reaction. Gaseous effluent was swept continuously via a fritted glass bubbler positioned at the bottom of the reactor vessel (i.e., immersed in the acid solution) into a chemiluminescence detector (Thermal Energy Analyzer Model 502LC, Thermedics, Inc., Woburn, Mass.). The area of the resulting chemiluminescence signal versus time curve was electronically computed and compared with that of a known quantity of nitric oxide gas standard to determine the amount of nitric oxide produced by acid treatment of the polymer aliquot.

This procedure was used to estimate the total amount of nitric oxide recoverable from the polymer. To estimate the rate of nitric oxide generation under physiological conditions, the inventive polymers were subjected to a procedure identical to that described above except that 2 ml of 10 mM phosphate buffer, pH 7.4, at 37° C. was injected into the reactor vessel in place of the sulfuric acid solution to start the reaction.

EXAMPLES

The preparation and characterization of biopolymers containing the nitric oxide-releasing $N_2O_2$ functional group are illustrated in the following examples:

Example I

This example illustrates the preparation of 1-(2S-carboxypyrrolidin-1-yl)-1-oxo-2-hydroxydiazene, disodium salt, as shown schematically as follows:

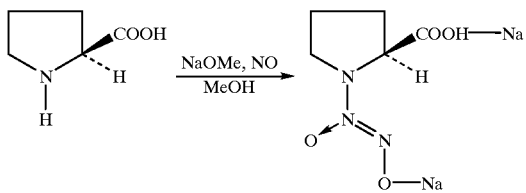

A solution of 10 g (0.087 mol) of L-proline in 39 ml (0.18 mol) of 25% sodium methoxide in methanol and 20 ml of methanol was degassed and exposed to 40 psi of NO for 20 h. The pressure was released and the solid residue was collected by filtration, washed with ether, and dried under vacuum to give 17 g of a white solid: UV (0.01 M NaOH) $\lambda_{max}$ ($\epsilon$) 250 nm ($\epsilon$=4.9 mM$^{-1}$ cm$^{-1}$); NMR (D$_2$O) δ1.71 (m, 1 H), 1.91 (m, 2 H), 2.27 (m, 1 H), 3.27–3.43 (m, 2 H), 4.04 (m, 1 H). A methanol peak was also present, but the solid was free of both proline and N-nitrosoproline.

Example II

This example illustrates the preparation of 1-hydroxy-2-oxo-3-carboxymethyl-3-methyl-1-triazene, disodium salt, as shown schematically as follows:

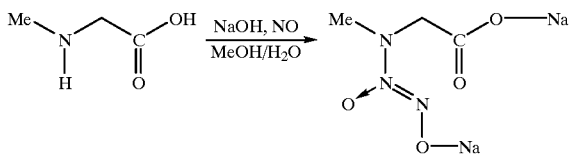

To a solution of 8 g (0.2 mol) of sodium hydroxide in 100 ml of methanol and 20 ml of water was added 8.9 g (0.1 mol) of sarcosine. The solution was charged with 40 psi of NO and stirred at 25° C. for 48 h. The pressure was released, and the solution was evaporated in vacuo to give a white solid: U $\lambda_{max}$ 250 nm. The distillate had a strong amine odor, which was determined to be methylamine on derivatization with benzoyl chloride.

The solid residue was dried under high vacuum, then analyzed by NMR in D$_2$O. Five products were detected by NMR: methylamine, δ2.28, 36%; 1-dimethylamino-1-oxo-2-hydroxydiazene, sodium salt, δ2.79, 15%; N-nitrosodimethylamine, δ3.11 and 3.91, 8%; N-nitrososarcosine, sodium salt, δ3.15 (s, E methyl), 3.84 (s, Z methyl), 4.21 (s, Z methylene), 4.80 (s, E methylene), 10%. The title compound was present as 32% of the mixture: δ3.11 (s, 3 H) and 3.60 (s, 2 H).

Example III

This example illustrates the preparation of 1-hydroxy-2-oxo-3-carboxymethyl-3-methyl-1-triazene N-methylamide, sodium salt, as shown schematically as follows:

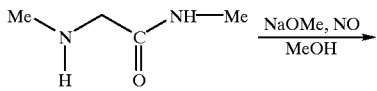

-continued

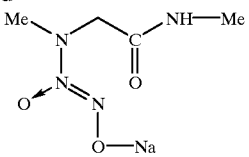

A solution of 150 ml (1.9 mol) of 40% aqueous methylamine was cooled to 0° C. To the solution was added 40 ml of 10 M sodium hydroxide followed by the careful addition over a 2-h period at 0° C. of α-chloroacetyl chloride (27 g, 0.24 mol).

Stirring was continued at room temperature overnight. The resulting solution was saturated with sodium chloride and extracted with dichloromethane, dried over sodium sulfate, and filtered through a layer of magnesium sulfate. Most of the solvent was removed on a rotary evaporator and the residue was distilled at 1 atm then under moderate vacuum. The product distilled at 90–2° C. at 125 mm Hg to yield 15 g (61%) of sarcosine N-methylamide: IR (film) 3318, 2952, 2889, 1659, 1553, 1462, 1413, 1166 cm$^{-1}$; NMR (CDCl$_3$) δ2.42 (s, 3 H), 2.86 (s, 1.5 H), 2.83 (s, 1.5 H), 3.23 (s, 2 H).

A solution of 1.7 g (0.0167 mol) of sarcosine N-methylamide in 3.5 ml (0.016 mol) of 25% sodium methoxide in methanol was placed in a pressure bottle, flushed with nitrogen and charged with 40 psi of nitric oxide. The solution was kept at 25° C. for 48 h, giving a thick paste. The pressure was released. The residue was washed with ether and dried under vacuum to give 1.4 g of a solid: UV $\lambda_{max}$ ($\epsilon$) 250 nm (2.4 mM$^{-1}$ cm$^{-1}$).

Example IV

This example illustrates the preparation of the bis(nitric oxide) adduct of L-prolyl-L-leucylglycinamide, as shown schematically as follows:

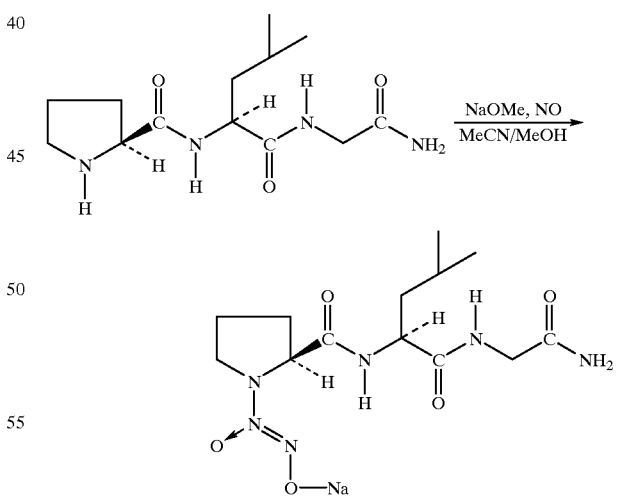

To a slurry of 120 mg (0.423 mmol) of L-prolyl-L-leucylglycinamide (Sigma) in 4 ml of acetonitrile was added 100 μl of 25% sodium methoxide in methanol. The resulting gel was treated with a few drops of methanol until a homogeneous solution was obtained. The solution was transferred into a micro-Parr bottle and bubbled with nitrogen for 5 min, followed by exposure to 40 psi of NO for 72 h. The reaction mixture was dried under vacuum to give 187 mg of a solid: $\lambda_{max}$ (ε) 250 nm (6.2 mM$^{-1}$ cm$^{-1}$) in pH 7.4 buffer. It released 0.86 moles of NO (per mole of tripeptide decomposed at this pH) with a half-life of 7 min at 37° C.

Oligopeptides and proteins of increasing chain length can be similarly derivatized with NO.

Example V

This example demonstrates the attachment of a nucleophilic center to a protein that does not contain a nucleophilic center that will readily react with NO, shown schematically as follows:

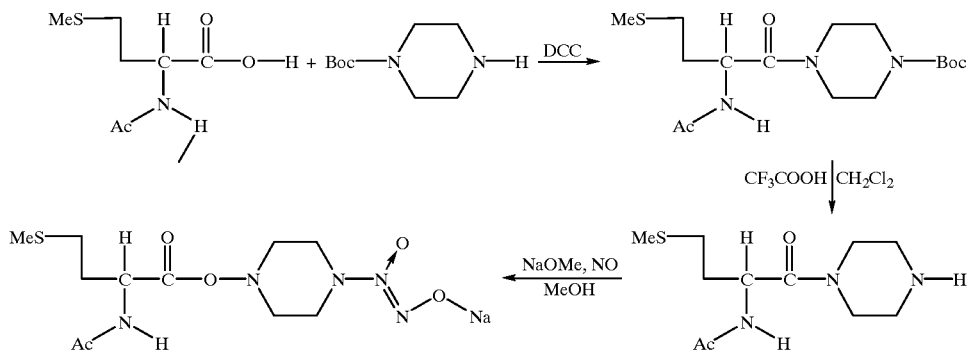

A solution of 4.78 g (0.025 mol) of N-acetyl-L-methionine in CH$_2$Cl$_2$: acetonitrile (120 ml) was cooled to 0° C. To this solution was added 5.36 g (0.025 mol) of dicyclohexylcarbodiimide (DCC) followed by the rapid addition of 3.90 g (0.021 mol) of N-t-butoxycarbonylpiperazine in 6 ml of dichloromethane. The progress of the reaction was followed on silica gel TLC plates developed with 4:1 acetonitrile: tetrahydrofuran and visualized with either iodine or ninhydrin spray. The reaction was complete within 2 h. A few drops of glacial acetic acid were added to the reaction mixture and the solvent was removed on a rotary evaporator. The residue was taken up in ether and filtered. The clear filtrate was washed with dilute acid followed by dilute base. The organic layer was separated, dried over anhydrous sodium sulfate, filtered, and evaporated to give 8.2 g of 1-(t-butoxycarbonyl)-4-(N-acetyl-L-methionyl)piperazine, a colorless oil which required no further purification: IR (film) 3304, 3058, 2973, 2931, 2868, 1701, 1645, 1539, 1420, 1237, 1173 cm$^{-1}$; NMR (CDCl$_3$) δ1.47 (s, 9 H), 1.80 (m, 2 H), 2.02 (s, 3 H), 2.10 (s, 3 H), 2.46 (m, 2 H), 3.53 (m, 8 H), 5.10 (M, 1 H), 6.35 (b, 0.5 H), 6.43 (b, 0.5 H).

To a solution of 8.6 g (0.024 mol) of 1-(t-butoxycarbonyl)-4-(N-acetyl-L-methionyl)piperazine in 60 ml of dichloromethane was added 10 ml of trifluoroacetic acid and the mixture was stirred at room temperature overnight. The solution was extracted with water and the resulting aqueous solution was made basic with sodium hydroxide. The product was extracted with dichloromethane, dried over sodium sulfate, and filtered. Evaporation of the solvent gave 2.1 g of 1-(N-acetyl-L-methionyl)piperazine, as an oil: IR (film) 3304, 3051, 2917, 2861, 1645, 1546, 1448, 1377 cm$^{-1}$; NMR (CDCl$_3$) δ1.95 (m, 2 H), 2.02 (s, 3 H), 2.10 (s, 3 H), 2.54 (m, 2 H), 2.98 (m, 4 H), 3.74 (m, 4 H), 5.10 (m, 1 H), 6.40 (b, 0.5 H), 6.48 (b, 0.5 H).

To a solution of 510 mg (1.97 mmol) of 1-(N-acetyl-L-methionyl)piperazine in 1 ml of methanol was added 428 μl (1.97 mmol) of 25% sodium methoxide in methanol. The system was degassed and charged with 40 psi of nitric oxide. After exposure of the solution to NO for 120 h, the pressure was released and the solid product was collected by filtration, washed with ether, and dried to give 27 mg of 1-[4-(N-acetyl-L-methionyl)piperazin-1-yl]-1-oxo-2-hydroxydiazene, sodium salt, as a white solid: UV $\lambda_{max}$ (ε) 252 nm (12.0 mM$^{-1}$ cm$^{-1}$). The product decomposed with a half-life of 6.9 min at pH 7 and 25° C. to produce 1.72 moles of NO per mole of test agent.

Example VI

This example demonstrates the attachment of a preformed NONOate containing a nucleophilic nitrogen atom to the C-terminus of a peptide, polypeptide or protein as shown schematically as follows:

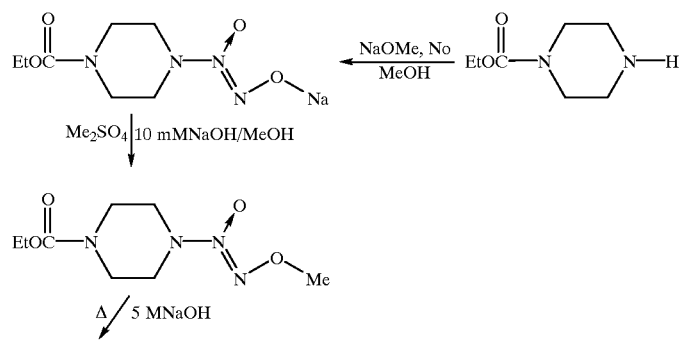

-continued

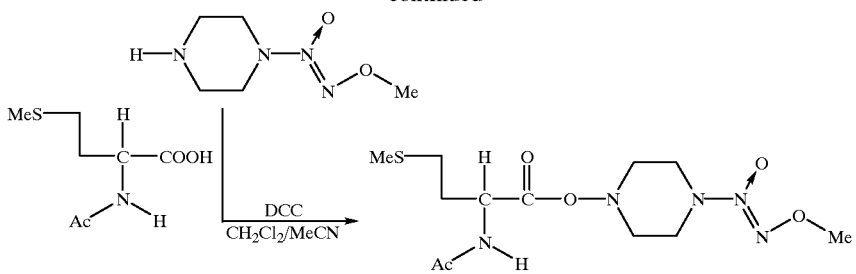

A solution of 20 g (0.126 mol) of ethyl 1-piperazinecarboxylate in 60 ml of methanol was placed in a Parr bottle. The solution was treated with 27.4 ml (0.126 mol) of 25% sodium methoxide in methanol. The system was evacuated, charged with 40 psi of nitric oxide and kept at 25° C. for 48 h. The white crystalline product was collected by filtration and washed with cold methanol as well as with copious amounts of ether. The product was dried under vacuum to give a 14.5 g (48%) yield of 1-(4-carbethoxypiperazin-1-yl)-1-oxo-2-hydroxydiazene, sodium salt: mp 184–5° C.; UV (0.01 M NaOH) $\lambda_{max}$ ($\epsilon$) 252 nm (10.4 mM$^{-1}$ cm$^{-1}$); NMR (D$_2$O) $\delta$1.25 (t, 3 H), 3.11 (m, 2 H), 3.68 (m, 2 H), 4.15 (q, 2 H). Anal Calcd. for C$_6$H$_{13}$N$_4$O$_4$Na: C, 35.00%; H, 5.42%; N, 23.33%; Na, 9.58%. Found: C, 34.87%; H, 5.53%; N, 23.26%; Na, 9.69%. The half-life of this compound at pH 7 and 25° C. was 5 min. This measurement was based on the loss of the 252-nm chromophore in the ultraviolet spectrum.

A solution of 1.3 g (5.4 mmol) of 1-(4-carbethoxypiperazin-1-yl)-1-oxo-2-hydroxydiazene, sodium salt, in 10 ml of 0.01 M aqueous sodium hydroxide was cooled in an ice bath. A solution of 2 ml of dimethyl sulfate in 10 ml of methanol was added dropwise. The resulting solution was stirred at 0° C. for 1 h, then allowed to warm gradually to room temperature. After 24 h the solution was concentrated on a rotary evaporator. The residue was extracted with dichloromethane, dried over sodium sulfate, and filtered through a layer of magnesium sulfate. The solvent was evaporated under reduced pressure and the residue was chromatographed on silica gel. Elution with 2:1 dichloromethane:ethyl acetate provided 683 mg (55%) of 1-(4-carbethoxypiperazin-1-yl)-1-oxo-2-methoxydiazene as an oil, which crystallized on standing: mp 46° C.; UV $\lambda_{max}$ ($\epsilon$) 240 nm (8.4 mM$^{-1}$ cm$^{-1}$); IR (film) 2988, 2945, 2875, 1707, 1504, 1068 cm$^{-1}$; NMR $\delta$3.38 (m, 4 H), 3.67 (m, 4 H), 4.03 (s, 3 H), 4.16 (q, 2 H); MS m/z (relative intensity, %), 232 (M$^+$, 3), 217 (16), 187 (10), 157 (100), 142 (5), 98 (4), 85 (27), 70 (26), 56 (94), 54 (19); exact mass calcd for C$_8$H$_{16}$N$_4$O$_4$ (M$^+$) 232.1171, found 232.1172. Anal Calcd for C$_8$H$_{16}$N$_4$O$_4$: C, 41.38%; H, 6.90%; N, 24.14%. Found C, 41.23%; H, 6.82%; N, 24.05%.

A mixture of 1.8 g (0.0078 mol) of 1-(4-carbethoxypiperazin-1-yl)-1-oxo-2-methoxydiazene and 20 ml of 5 M aqueous sodium hydroxide was heated at reflux. After 45 min no starting material remained in the mixture, as assessed from qualitative thin layer chromatography. The solution was allowed to cool to room temperature and evaporated to a viscous residue, which was extracted with ethyl acetate, dried over sodium sulfate, filtered, and evaporated. The product was chromatographed on silica gel and eluted with 1:1 dichloromethane:acetone giving 820 mg (66%) of 1-(piperazin-1-yl)-1-oxo-2-methoxydiazene as a pale yellow oil: UV $\lambda_{max}$ ($\epsilon$) 234 nm (7.0 mM$^{-1}$ cm$^{-1}$); NMR $\delta$3.03 (m, 4 H), 3.38 (m, 4 H), 4.06 (s, 3 H); IR (film) 3318, 2945, 2854, 1447, 1364, 1286, 1230, 1046, 1004 cm$^{-1}$; MS m/z (relative intensity, %) 160 (M$^+$, 2), 145 (7), 143 (10), 115 (9), 85 (56), 58 (7), 56 (100); exact mass calcd for C$_5$H$_{12}$N$_4$O$_2$ (M$^+$) 160.0960, found 160.0966.

To a solution of 164 mg (0.856 mmol) of N-acetyl-L-methionine in 10 ml of 1:1 dichloromethane:acetonitrile was added 206 mg (1 mmol) of dicyclohexylcarbodiimide (DCC) followed by the rapid introduction of 137 mg (0.856 mmol) of 1-(piperazin-1-yl)-1-oxo-2-methoxydiazene in 3 ml of dichloromethane. The reaction mixture was stirred at 25° C. for 4 h. A few drops of glacial acetic acid were added to decompose excess DCC. The mixture was filtered and evaporated. The residue was extracted with ethyl acetate, which in turn was washed with dilute hydrochloric acid, followed by dilute aqueous sodium hydroxide. The organic layer was dried over sodium sulfate, filtered through a layer of magnesium sulfate, and evaporated in vacuo. Purification of 1-(4-[N-acetyl]-L-methionylpiperazin-1-yl)-1-oxo-2-methoxydiazene was accomplished on silica gel using 4:1 acetonitrile:tetrahydrofuran as the eluant: UV $\lambda_{max}$ ($\epsilon$) 230 nm (8.7 mM$^{-1}$ cm$^{-1}$); NMR $\delta$2.02 (s, 3 H), 2.07 (m, 2 H), 2.11 (s, 3 H), 3.46 (m, 4 H), 3.83 (m, 4 H), 4.03 (s, 3 H), 5.15 (m, 1 H), 6.28 (b, 0.5 H), 6.35 (b, 0.5 H); IR 3297, 2931, 2847, 1645, 1546, 1497, 1441, 1223 cm$^{-1}$; MS m/z (relative intensity, %), 333 (M$^+$, 4), 318 (2), 304 (3), 303 (16), 288 (12), 260 (11), 259 (100), 258 (9), 214 (78), 184 (37), 183 (10), 174 (5), 146 (26), 142 (56), 141 (5), 104 (63), 61 (60); exact mass calcd for C$_{12}$H$_{23}$N$_5$O$_4$S (M$^+$) 333.1470, found 333.1471.

All publications, patents, and patent applications cited herein are hereby incorporated by reference to the same extent as if each individual document were individually and specifically indicated to be incorporated by reference and were set forth in its entirety herein.

While this invention has been described with emphasis upon preferred embodiments, it will be obvious to those of ordinary skill in the art that the preferred embodiments may be varied. It is intended that the invention may be practiced otherwise than as specifically described herein. Accordingly, this invention includes all modifications encompassed within the spirit and scope of the appended claims.

We claim:

1. A polymeric composition capable of releasing nitric oxide, said composition comprising (i) a biopolymeric backbone wherein said backbone is of a tissue-specific antibody or fragment thereof, a cell-specific antibody or fragment thereof, a tumor-specific antibody or fragment thereof, a protein containing a recognition sequence for a receptor-ligand interaction favorable to cell or tissue selective attachment, wherein said backbone includes at least one amino group or at least one carboxyl group or combinations thereof, and (ii) at least one nitric oxide-releasing $N_2O_2^-$ functional group selected from the group consisting of [X[(O)NO]] X[N(O)NO] and [N(O)NO]X, wherein X is a nucleophilic or electrophilicorganic residue covalently bonded to said $N_2O_2^-$ functional group, and wherein the $N_2O_2^-$ functional group is covalently bound to said polymeric composition at one or more of said amino group or said carboxyl group through said nucleophilic or electrophilic organic residue.

2. The polymeric composition of claim 1, wherein said nitric oxide-releasing $N_2O_2^-$ functional group is of the formula:

(I)

wherein J is an inorganic moiety or an organic moiety selected from the group consisting of $C_1$–$C_{12}$ aliphatic, $C_3$–$C_8$ cycloalkyl, benzyl, phenyl, substituted benzyl, substituted phenyl, benzylcarbonyl, phenylcarbonyl, substituted benzylcarbonyl, substituted phenylcarbonyl, $C_1$–$C_{12}$ acyl, and

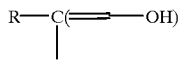

wherein R is $C_1$–$C_{12}$ aliphatic, $C_3$–$C_8$ cycloalkyl, benzyl, phenyl, substituted benzyl or substituted phenyl, and said substituted benzyl and substituted phenyl is substituted with one or two substituents selected from the group consisting of halogen, hydroxy, $C_1$–$C_4$ alkyl, $C_1$–$C_4$ alkoxy, amino, mono $C_1$–$C_4$ alkylamino, di $C_1$–$C_4$ alkyl-amino, phenyl and phenoxy, $M^{+x}$ is a pharmaceutically acceptable cation, where x is the valence of the cation, a is one or two, and b and c are the smallest integers that result in a neutral compound.

3. The method of claim 2, wherein J is a moiety which is linked to the nitrogen of the remainder of the complex through an atom other than a carbon atom.

4. The polymeric composition of claim 2, wherein the nitric-oxide releasing group is a compound other than a salt of alanosine or dopastin.

5. The polymeric composition of claim 1, wherein said nitric oxide-releasing $N_2O_2^-$ functional group is of the formula:

(II)

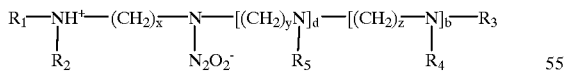

wherein b and d are the same or different and may be zero or one, $R_1$, $R_2$, $R_3$, $R_4$, and $R_5$ are the same or different and may be hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, and x, y, and z are the same or different and are integers from 2 to 12.

6. The polymeric composition of claim 1, wherein said nitric oxide-releasing $N_2O_2^-$ functional group is of the formula:

(III)

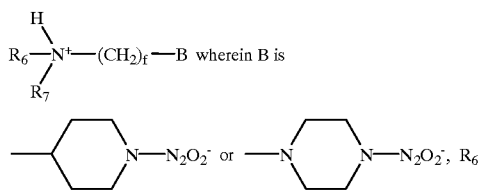

and $R_7$ are the same or different and may be hydrogen, $C_{3-8}$ cycloalkyl, $C_{1-2}$ straight or branched chain alkyl, benzyl, benzoyl, phthaloyl, acetyl, trifluoroacetyl, p-toluyl, t-butoxycarbonyl, or 2,2,2-trichloro-t-butoxycarbonyl, f is an integer from 0 to 12, with the proviso that when B is the substituted piperazine moiety

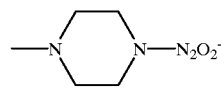

then f is an integer from 2 to 12.

7. The polymeric composition of claim 1, wherein said nitric oxide-releasing $N_2O_2^-$ functional group is of the formula:

(IV)

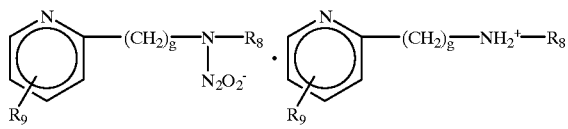

wherein $R_8$ is hydrogen, $C_{3-8}$ cycloalkyl, $C_{1-12}$ straight or branched chain alkyl, benzyl, benzoyl, phthaloyl, acetyl, trifluoroacetyl, p-toluyl, t-butoxycarbonyl, or 2,2,2-tri-chloro-t-butoxycarbonyl, $R_9$ is hydrogen or a $C_{1-12}$ straight or branched chain alkyl, and g is 2 to 6.

8. The polymeric composition of claim 1, wherein said nitric oxide-releasing $N_2O_2^-$ functional group is of the formula:

(V)

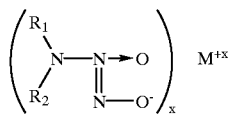

wherein $R_1$ and $R_2$ are independently selected from the group consisting of a straight chain or branched chain $C_1$–$C_{12}$ alkyl group and a benzyl group, or else $R_1$ and $R_2$ together with the nitrogen atom they are bonded to form a heterocyclic group, a pyrrolidino, piperidino, piperazino or morpholino group, $M^{+x}$ is a pharmaceutically acceptable cation, and x is the valence of the cation.

9. The polymeric composition of claim 1, wherein said nitric oxide-releasing $N_2O_2^-$ functional group is of the formula:

$$K[(M)_{x'}(L)_y(R^1R^2N-N_2O_2)_z]$$ (VI)

wherein M is a pharmaceutically acceptable metal, or, where x is at least two, a mixture of two different pharmaceutically acceptable metals, L is a ligand different from ($R^1R^2N$—$N_2O_2$) and is bound to at least one metal, $R^1$ and $R^2$ are each organic moieties and may be the same or different, x is an integer of from 1 to 10, x' is the formal oxidation state of the metal M, and is an integer of from 1 to 6, y is an integer of from 1 to 18, and where y is at least 2, the ligands L may be the same or different, z is an integer of from 1 to 20, and K is a pharmaceutically acceptable counterion to render the compound neutral to the extent necessary.

10. The polymeric composition of claim 1, wherein said nitric oxide-releasing $N_2O_2^-$ functional group is of the formula:

[R—N(H)N(NO)O—]$_y$X    (VII)

wherein R is $C_{2-8}$ lower alkyl, phenyl, benzyl, or $C_{3-8}$ cycoloalkyl, any of which R groups may be substituted by one to three substituents, which are the same or different, selected from the group consisting of halo, hydroxy, $C_{1-8}$ alkoxy, —$NH_2$, —C (O) $NH_2$, —CH(O), —C(O) OH, and —$NO_2$, X is a pharmaceutically acceptable cation, a pharmaceutically acceptable metal center, or a pharmaceutically acceptable organic group selected from the group consisting of $C_{1-8}$ lower alkyl, —C(O)CH$_3$, and —C(O)NH$_2$, and y is one to three, consistent with the valence of X.

11. The polymeric composition of claim 1, wherein said nitric oxide-releasing $N_2O_2^-$ functional group is of the formula:

(VIII)

wherein $R_1$ and $R_2$ are independently chosen from $C_{1-12}$ straight chain alkyl, $C_{1-12}$ alkoxy or acyloxy substituted straight chain alkyl, $C_{2-12}$ hydroxy or halo substituted straight chain alkyl, $C_{3-12}$ branched chain alkyl, $C_{3-12}$ hydroxy, halo, alkoxy, or acyloxy substituted branched chain alkyl, $C_{3-12}$ straight chain olefinic and $C_{3-12}$ branched chain olefinic which are unsubstituted or substituted with hydroxy, alkoxy, acyloxy, halo or benzyl, or $R_1$ and $R_2$ together with the nitrogen atom to which they are bonded form a heterocyclic group, a pyrrolidino, piperidino, piperazino or morpholino group, and $R_3$ is a group selected from $C_{1-12}$ straight chain and $C_{3-12}$ branched chain alkyl which are unsubstituted or substituted by hydroxy, halo, acyloxy or alkoxy, $C_{2-12}$ straight chain or $C_{3-12}$ branched chain olefinic which are unsubstituted or substituted by halo, alkoxy, acyloxy or hydroxy, $C_{1-12}$ unsubstituted or substituted acyl, sulfonyl and carboxamido; or $R_3$ is a group of the formula —(CH$_2$)$_n$—ON=N(O)NR$_1$R$_2$, wherein n is an integer of 2–8, and $R_1$ and $R_2$ are as defined above; with the proviso that $R_1$, $R_2$ and $R_3$ do not contain a halo or a hydroxy substituent α to a heteroatom.

12. A pharmaceutical composition comprising a pharmaceutically acceptable carrier and the polymeric composition of claim 1.

13. A pharmaceutical composition comprising a pharmaceutically acceptable carrier and the polymeric composition of claim 2.

14. A pharmaceutical composition comprising a pharmaceutically acceptable carrier and the polymeric composition of claim 3.

15. A pharmaceutical composition comprising a pharmaceutically acceptable carrier and the polymeric composition of claim 4.

16. A pharmaceutical composition comprising a pharmaceutically acceptable carrier and the polymeric composition of claim 5.

17. A pharmaceutical composition comprising a pharmaceutically acceptable carrier and the polymeric composition of claim 6.

18. A pharmaceutical composition comprising a pharmaceutically acceptable carrier and the polymeric composition of claim 7.

19. A pharmaceutical composition comprising a pharmaceutically acceptable carrier and the polymeric composition of claim 8.

20. A pharmaceutical composition comprising a pharmaceutically acceptable carrier and the polymeric composition of claim 9.

21. A method of treating a biological disorder in a mammal in which dosage with nitric oxide is therapeutic, comprising administering to said mammal a polymeric composition capable of releasing nitric oxide, said composition comprising a biopolymeric backbone wherein said backbone is a protein, wherein said backbone includes at least one amino group or at least one carboxyl group or combinations thereof, and a nitric oxide-releasing $N_2O_2^-$ functional group selected from the group consisting of X[N(O)NO] and [N(O)NO]X, wherein X is a nucleophilic or electrophilic organic residue covalently bonded to said $N_2O_2^-$ functional group, and wherein the $N_2O_2^-$ functional group is covalently bound to said biopolymer at one or more of said amino group or said carboxyl group in an amount sufficient to release a therapeuticallyeffective amount of nitric oxide.

22. A method of treating a biological disorder in a mammal in which dosage with nitric oxide is therapeutic, comprising administering the polymeric composition of claim 2 in an amount sufficient to release a therapeutically effective amount of nitric oxide.

23. A method of treating a biological disorder in a mammal in which dosage with nitric oxide is therapeutic, comprising administering the polymeric composition of claim 3, in an amount sufficient to release a therapeutically effective amount of nitric oxide.

24. A method of treating a biological disorder in a mammal in which dosage with nitric oxide is therapeutic, comprising administering the polymeric composition of claim 4 in an amount sufficient to release a therapeutically effective amount of nitric oxide.

25. A method of treating a biological disorder in a mammal in which dosage with nitric oxide is therapeutic, comprising administering the polymeric composition of claim 5 in an amount sufficient to release a therapeutically effective amount of nitric oxide.

26. A method of treating a biological disorder in a mammal in which dosage with nitric oxide is therapeutic, comprising administering the polymeric composition of claim 9 in an amount sufficient to release a therapeutically effective amount of nitric oxide.

27. A method of treating a biological disorder in a mammal in which dosage with nitric oxide is therapeutic, comprising administering the polymeric composition of claim 7 in an amount sufficient to release a therapeutically effective amount of nitric oxide.

28. A method of treating a biological disorder in a mammal in which dosage with nitric oxide is therapeutic, comprising administering the polymeric composition of claim 8 in an amount sufficient to release a therapeutically effective amount of nitric oxide.

29. A method of treating a biological disorder in a mammal in which dosage with nitric oxide is therapeutic, comprising administering the polymeric composition of claim 9 in an amount sufficient to release a therapeutically effective amount of nitric oxide.

30. A method of treating a biological disorder in a mammal in which dosage with nitric oxide is therapeutic, comprising administering to said mammal the polymeric composition of claim 1 in an amount sufficient to release a therapeutically effective amount of nitric oxide.

\* \* \* \* \*